United States Patent [19]

Jansen et al.

[11] Patent Number: 4,459,357

[45] Date of Patent: Jul. 10, 1984

[54] PROCESS AND APPARATUS FOR THE QUANTITATIVE DETERMINATION OF CATIONS OR ANIONS BY ION CHROMATOGRAPHY

[76] Inventors: Karl-Heinz Jansen, Jahnstrasse 14, 8034 Germering; Karl-Heinz Fischer, Am Kochberg 14, 6457 Maintal; Bernhard Wolf, Narzissenstrasse 4, 8031 Puchheim, all of Fed. Rep. of Germany

[21] Appl. No.: 393,479

[22] Filed: Jun. 29, 1982

[30] Foreign Application Priority Data

Jul. 8, 1981 [DE] Fed. Rep. of Germany ....... 3126860

[51] Int. Cl.$^3$ ............................................. G01N 31/08
[52] U.S. Cl. ................................ 436/161; 204/180 P; 210/656; 422/70
[58] Field of Search .............. 204/180 P, 302; 422/68, 422/70, 90; 73/61.1 C; 436/161, 178, 150; 210/656

[56] References Cited

U.S. PATENT DOCUMENTS

| | | | |
|---|---|---|---|
| 2,794,777 | 6/1957 | Pearson | 204/180 P X |
| 2,921,005 | 1/1960 | Bodamer | 204/180 P X |
| 3,244,620 | 4/1966 | Hansen et al. | 204/180 P X |
| 3,925,019 | 12/1975 | Small et al. | 436/150 X |
| 4,149,957 | 4/1979 | Gibson et al. | 204/180 P X |
| 4,272,246 | 6/1981 | Fritz et al. | 436/161 X |

FOREIGN PATENT DOCUMENTS 0032770  7/1981  European Pat. Off. .

*Primary Examiner*—Arnold Turk
*Attorney, Agent, or Firm*—Larson and Taylor

[57] ABSTRACT

A procedure and an apparatus for the quantitative determination of cations and anions by ion chromatography is described which can be used, for example, to test drinking water, river water or water in drains. The sample is injected into a buffer stream which comes through a chromatography column. The eluate from the column is measured in a conductivity detector, the background being suppressed in a new cell. The cell consists of two ion exchange membranes which are not permeable to the ions to be measured and two electrodes which set up an electric field across the membranes. The highly dissociated ions of opposite charge in the eluate are exchanged into compounds of low conductivity and removed from the cell.

16 Claims, 1 Drawing Figure

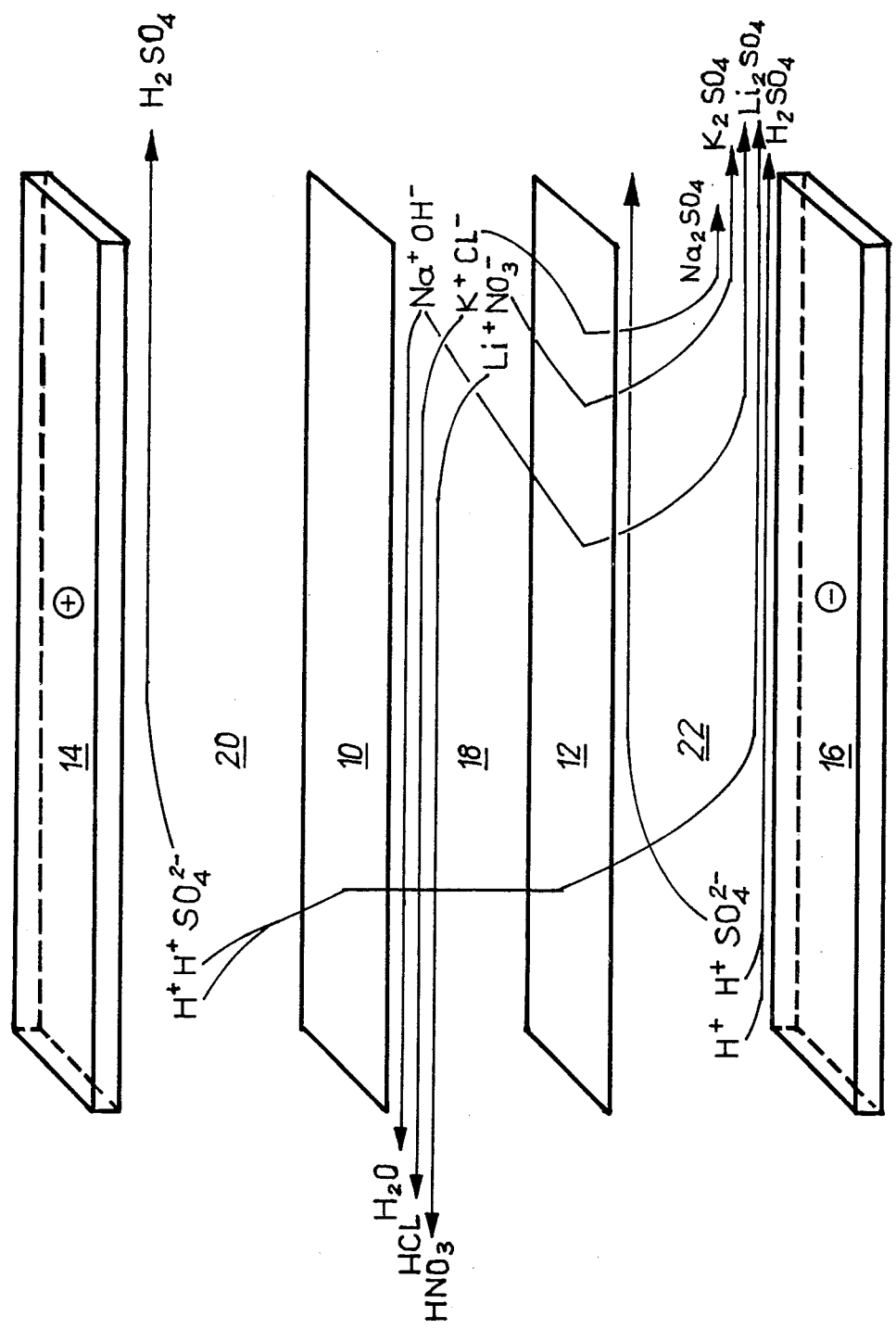

PROCESS AND APPARATUS FOR THE QUANTITATIVE DETERMINATION OF CATIONS OR ANIONS BY ION CHROMATOGRAPHY

FIELD OF THE INVENTION

The invention concerns a procedure and an apparatus for the quantitative determination of anions or cations in a sample using ion chromatography, whereby a sample (containing the ions to be determined) is injected into and then carried by a buffer stream onto a chromatography column; the background ions in the eluate from the column are suppressed by an ion exchange mechanism and the determination is by conductivity measurements.

BACKGROUND OF THE INVENTION

The invention begins with the current state of the technology as described, for example, in DE-OS No. 24 37 600. There the basic problem, that the eluant has such a high conductivity that measuring the conductivity of the ion species separated in the chromatography column is impossible, is solved by connecting to the latter a suppressor column of opposite ion exchange type as to the chromatography column. In the suppressor column the ion species passing the ions to be determined are exchanged for $OH^-$ or $H^+$ ions. The disadvantage of this system is that the suppressor column can *not* be run continuously as the column must be periodically regenerated. In addition, the effect of the suppressor column varies with use and is dependent on chemical properties such as pH, diffusions, adsorption and exchange effects, all of which will reduce the reproducibility and exactness of the analyses.

SUMMARY OF THE INVENTION

The invention enables the suppressor reaction to be dramatically improved, so that the analysis can be carried out continuously under constant chemical conditions. To do this, the background ions from the chromatography column are suppressed by an ion exchange mechanism and the determination is by conductivity measurements.

To suppress the background ions the eluate is passed between two ion exchange membranes which are not permeable to ions, of opposite charge to those which are to be determined. Two electrodes are so arranged that an electric field can be set up across the direction of flow so that strongly dissociated electrolytes (in similar or quite different solutions) can be separated from each other between the electrodes and the ion exchange membrane. Under the influence of the electric field the weakly dissociated ions of low conductivity in the buffer are carried through, whilst the buffer ions of opposite charge are removed after passing through the membrane into the electrolytic solution.

BRIEF DESCRIPTION OF THE DRAWING

The single FIGURE is a schematic exploded perspective view of the components of a cell according to the present invention.

DETAILED DESCRIPTION OF THE PREFERRED EMBODIMENTS

The invention consists of a procedure and an apparatus as follows: storage for the buffers, a sample inject valve, a chromatography column filled with ion exchange resin, a second ion exchange device to suppress the background ions, and a conductivity cell. The second ion exchange device for suppressing background ions consists of a channel for the eluate which is at least partially partitioned by ion exchange membranes on the outside of which are electrolyte solutions and the adjacent spaces contain electrodes which can set up an electric field across the eluate channel.

Before going into the background of the various chemical methods to analyse anions and cations, we should look more closely at the cell (see diagram) to obtain a better understanding of the nature of the invention. The cell consists of two ion exchange membranes (10,12) which are fixed between two platinum electrodes (14,16) attached to the side walls of the cell (not shown in diagram). The eluate from the separation column flows through the channel marked 18 on the diagram. The platinum electrodes (14,16) are connected to a potential which can be set to between 50 and 550 Volts which leads to currents of between 10 mA and 1.2 A. In the main a current of 120 mA is obtained running at 200 Volts.

The distance between the electrodes (14,16) and the adjacent ion exchange membranes (10 or 12) is between ca. 4 mm and ca. 50 mm, often more than not 8 mm. The two membranes are usually between ca. 0.1 mm and ca. 3 mm apart. The two ion exchange membranes and the electrodes are pressure stable up to 30 bar (at the moment), so that they form in cross section three square channels, i.e. on either side of the eluate channel (18) there are side channels formed by the membrane and the anode electrode (14)—channel 20—and channel 22 between the cathode (16) and membrane (12).

The two side channels have electrolytic solutions pumped through them which act as electrode buffers. Both these buffers have to be pumped from different buffer reservoirs in quite separate circulation channels through the side channels. The chemical and physical composition of the two electrode buffers is sometimes identical but often different.

The chemical reactions in the cell are dependent on
  the type and condition of the ion exchange membranes (10,12)
  the nature and concentration of the electrode buffers and the eluate The voltage across the electrodes and the resulting flow rates only influence the reaction time and not the reaction as such.

In practice a length of ca. 100–500 mm (normally 270 mm) for the membranes and a thickness of ca. 0.4–5 mm (normally 1 mm) has been found to be best. The materials to be used for the membrane and the solutions are determined by which type of ions, anions or cations, are to be measured. For the analysis of anions, cations exchange membranes are used (consisting of a vinylchloride or teflon matrix with $SO_3$ groups on the surface) whose thickness varies from 0.09–0.2 mm (usually 0.12 mm) and which have an electrical resistance of ca. 2.0–5.9 ohm/cm$^2$. As the electrode buffer the strongly dissociated mineral acids, mainly $H_2SO_4$, $HNO_3$ and $H_3PO_3$ in concentrations from 0.001 to 1 mole/l are used. These electrode buffer flow in the side channels (20,22) in the opposite direction to the eluate flow in the central channel (18).

The eluant chosen for the buffer system of the separation column depends on the ions to be separated. In addition, for cation exchange (with $H^+$ ions) the eluant must produce either demineralized water or a weakly dissociated compound of low conductivity (e.g.

$H_2CO_3$) after the exchange. Some examples are given below.

The reaction in the cell for anion determination is shown in the diagram using a concrete example. Chloride and nitrate are to be separated on the ion exchange column using NaOH as eluant. The anions are present in the sample as potassium and lithium salts respectively. KCl and $LiNO_3$ will flow into the cell from the column but because of the background from the NaOH identification of the anions by conductivity measurements or similar methods is not possible.

The flow rate of the eluate through the cell is approximately 2 ml/min. i.e. with a cell volume of 200 $\mu$l there will be an average dwell time of 0.1 min. In the side channels 0.15 molar $H_2SO_4$ is flowing as electrode buffer at a rate of 0.1 ml/min. Under the influence of the potential of 300 V the hydronium ions built-up in the region of the anode will flow to the cathode. As the cation exchange membrane is permeable to cations but not to anions (transport No. 0.97) the $SO_4^=$ ions cannot move from the anion region to the cation region. The ions in the eluate stream undergo a parallel process. There is no volume mixing as the membranes are also not permeable as far as the solutions are concerned. The anions in the eluate stream would move in channel 18 towards the anode but cannot penetrate the cation exchange membrane 10, so that they are carried quantitatively with the eluate into the detector cell. The cations in the eluate stream will move through the cation exchange membrane 12 to the cathode 16 (in channel 22) and will be replaced by hydronium ions. The velocity of the movement will be effected by the electrical potential and the resulting rate of the flow. In addition the overriding factor will be the osmotic pressure. This can be optimized by reducing the molar concentration of the electrode buffer in channel 22 and increasing the flow rate in this channel. A reduction of the $H_2SO_4$ concentration to $5 \times 10^{-3}$ mol/l with a flow rate of 0.5 ml/min produces no deterioration in the cell measurements but much increased base line stability in the conductivity detector.

The reactions can be summarized as follows:
(a) in the region of the anode
  1. Dissociation of the $H_2SO_4$ $$H_2SO_4 \rightleftharpoons 2H^+ + SO_4^{2-}$$

and also (see Brömsted—

$$H_2SO_4 + H_2O \rightleftharpoons 2H_3O^+ + SO_4^{2-}$$

2. The $H^+$ ions (protons) and the $H_3O^+$ (hydronium ions) will move through the cation exchange membrane into the eluate stream.
  The sulphate ions move in the direction of the anode 14 and are washed out of the system.
(b) in the eluate channel 18
  1. Dissociation of NaOH, KCl, $LiNO_3$ $$NaOH + KCl + LiNO_3 \rightleftharpoons Na^+ + K^+ + Li^+ + OH^- + Cl^- + NO_3^-$$

2. A movement of the cations $Na^+$, $Li^+$ and $K^+$ in the direction of the cathode 16 through the cation exchange membrane 12.
  A movement of the anions in the direction of the anode 14 along the non-permeable cation exchange membrane in the direction of flow causes the anions to react with the abundance of $H_3O^+$ ions present.

$$Cl^- + NO_3^- + OH^- + 3 H_3O^+ \rightleftharpoons HCl + HNO_3 + 4H_2O$$

i.e. the eluant, NaOH, of high conductivity will react to form a compound of low conductivity ($H_2O$) and the samples (KCl, $LiNO_3$) will react to form compounds (HCl, $HNO_3$) of high conductivity.
(c) in the region of the cathode 22
  1. Dissociation of $H_2SO_4$ as above
  2. A movement of hydronium ions and cations from the eluate towards the cathode 16 and hence out of the system. A movement of the sulphate ions in the direction of the anion as far as the cation exchange membrane and then along the membrane and out of the system.

For the determination of cations, anion exchange membranes are used. These consist of a matrix of polyvinylchloride or fluorcarbons (polytetrafluoroethylene and polyperfluoethylene-propylene) with ammonium—$NH_4^+$ ions on the surface. The membrane thickness is normally between 0.11 and 0.15 mm and its electrical resistance is between ca. 2.4 and 4.6 ohm/cm². The electrode buffer is normally NaOH or similar bases in concentrations between 0.001 and 1 mole/l. The buffer flows through channels 20 and 22.

The eluant acids used, depend upon the ions to be analysed. The overriding consideration is that such acids (e.g. HCl or $H_2SO_4$) must result in demineralized water or other weakly dissociated compounds after exchange of the anions with $OH^-$.

In the determination of cations, the movements of the ions are analogous to the description above in that the $OH^-$ ions from the cathode region and the anions in the eluate stream move to the anode through the anion exchange membrane, whereas the cations are held in their channels by the membrane.

Finally a few examples of the method are given below:

| Type of analysis | Eluant | Flushing Ion | Reaction Product |
|---|---|---|---|
| Anion determination | NaOH | $H^+$ | $H_2O$ |
| " | $NaHCO_3$ | $H^+$ | $H_2CO_3$ |
| " | $Na_2CO_3$ | $H^+$ | $H_2CO_3$ |
| " | $Na_2B_4O_7$ | $H^+$ | $H_3BO_3$ |
| Cation determination | HCl | $OH^-$ | $H_2O$ |
| " | $H_3PO_4$ | $OH^-$ | $H_2O$ |
| " | $HNO_3$ | $OH^-$ | $H_2O$ |
| " | $H_2SO_4$ | $OH^-$ | $H_2O$ |
| " | R-ammonium hydrochloride | $OH^-$ | R-ammonium hydroxide |

As the above table demonstrates, the method described using the new cell with ion exchange membranes results in the strongly dissociated compounds of high conductivity used as eluants being turned into weakly dissociated compounds of low conductivity in all cases which will not affect the quantitative measurement, by conductivity, of the cations or anions in the sample.

We claim:

1. A method for quantitatively determining cations or anions in a solution by ion chromatography comprising the steps of:
   injecting a sample of the solution into a buffer stream;
   conducting the sample containing buffer stream onto a chromatography column;
   suppressing the background ions in the eluate from the column by passing the eluate through a cell including (a) two ion exchange membranes which are impermeable to ions of the same charge as those to be determined, (b) two electrodes spaced on opposite sides of the membranes and generating an electric field across the direction of flow of the eluate, and (c) a first and a second electrolytic solution flowing in the respective spaces between the adjacent electrodes and membranes, such that in the eluate one ion of the strongly dissociated electrolyte forms water or a weakly dissociated electrolyte of low conductivity while, under the influence of the electric field, the other ion of opposite charge of the strongly dissociated electrolyte passes through one of said membranes and is removed by the electrolyte solution of the other side of this membrane; and
   measuring the conductivity of the eluate from the cell to determine cations or anions.

2. A method as claimed in claim 1 wherein the electrolytic solutions have a concentration of electrolyte of between 0.001 to 1 mol/l.

3. A method as claimed in claims 1 or 2 wherein the quantitative determination is made for anions and acidic electrolytic solutions are used in the spaces between adjacent electrodes and membranes.

4. A method as claimed in claims 1 or 2 wherein the quantitative determination is made for cations and basic electrolytic solutions and are used between adjacent electrodes and membranes.

5. A method as claimed in claim 3 in which the ion exchange membranes are cation exchange membranes comprising a polyvinyl-chloride or fluorocarbon matrix with $SO_3^-$ groups attached for the determination of anions.

6. A method as claimed in claim 4 in which the ion exchange membranes are anion exchange membranes comprising a polyvinyl-chloride or fluorocarbon matrix with $NH_4^+$ groups attached for the determination of cations.

7. A method as claimed in claims 1 or 2 wherein the electrolytic solutions flow opposite to the eluate in the cell.

8. An apparatus for quantitatively determining cations or anions in a solution by ion chromatography comprising:
   a chromatography column filled with an ion exchange resin and through which a buffer solution containing a sample of the solution to be determined is passed;
   an ion exchange cell means through which the eluate from said chromatography column is passed for suppressing the background ions contained in the eluate, said ion exchange cell means including a longitudinal channel through which the eluate is passed, a pair of ion exchange membranes located along opposite lateral portions of said channel, an electric field generating means for generating an electric field across said channel and including an anode electrode spaced outwardly from one said membrane and said central channel to form a first space and a cathode electrode spaced outwardly from said other membrane and said central channel to form a second space, said spaces permitting electrolytic solution flow between said electrodes and said adjacent membranes; and
   a conductivity cell means to which the eluate from said ion exchange cell means is conducted for measuring the conductivity of the eluate and hence quantitatively determining cations or anions.

9. An apparatus as claimed in claim 8 wherein the lateral distance between said ion exchange membranes is approximately 0.1 to 3 mm.

10. An apparatus as claimed in claim 9 wherein the distance between a respective said electrode and a respective said adjacent ion exchange membrane is approximately 4 to 50 mm.

11. An apparatus as claimed in claim 10 wherein the distance between a respective said electrode and a respective said adjacent ion exchange membrane is approximately 8 mm.

12. An apparatus as claimed in claim 8 wherein each respective electrode defines a wall of said respective space in which said electrolyte solutions are located.

13. An apparatus as claimed in claim 2 wherein said channel and said spaces are square in lateral cross section.

14. An apparatus as claimed in claims 8 wherein said electrodes are made of platinum.

15. An apparatus as claimed in claim 8 wherein said ion exchange membranes comprise a polyvinylchloride or fluorocarbon matrix containing surface ions selected from the group consisting of $SO_3^-$ for the determination of anions and $NH_4^+$ for the determination of cations.

16. An apparatus as claimed in claim 15 wherin the thickness of said ion exchange membranes is approximately 0.09 to 0.2 mm.

* * * * *